United States Patent [19]

Passaro et al.

[11] Patent Number: 4,692,621

[45] Date of Patent: Sep. 8, 1987

[54] DIGITAL ANESTHETIC AGENT ANALYZER

[75] Inventors: Robert E. Passaro, Richmond; Kevin G. Williams, Pinole; George K. Parnoff, Walnut Creek; Raymond E. Rogers, Oakland, all of Calif.

[73] Assignee: Andros Anlayzers Incorporated, Berkeley, Calif.

[21] Appl. No.: 786,736

[22] Filed: Oct. 11, 1985

[51] Int. Cl.$^4$ ............................................. G01N 21/35
[52] U.S. Cl. .................................. 250/343; 250/252.1; 250/339; 356/437
[58] Field of Search ............ 250/351, 339, 343, 252.1; 356/439, 438, 437

[56] References Cited

U.S. PATENT DOCUMENTS

| | | | |
|---|---|---|---|
| 3,790,797 | 2/1974 | Sternberg et al. | 250/345 |
| 3,893,770 | 7/1975 | Takami et al. | 356/328 |
| 3,898,462 | 8/1975 | Ishida et al. | 250/344 |
| 3,953,734 | 4/1976 | Dimeff | 250/343 |
| 4,011,859 | 3/1977 | Frankenberger | 128/719 |
| 4,013,260 | 3/1977 | McClatchie et al. | 250/343 |
| 4,110,619 | 8/1978 | Zörner | 250/344 |
| 4,153,837 | 5/1979 | Ross | 250/343 |
| 4,204,768 | 5/1980 | N'Guyen | 356/243 |
| 4,281,248 | 7/1981 | Fabinski et al. | 250/345 |
| 4,346,296 | 8/1982 | Passaro et al. | 250/343 |
| 4,423,739 | 1/1984 | Passaro et al. | 128/719 |
| 4,480,190 | 10/1984 | Burough et al. | 250/343 |
| 4,549,080 | 10/1985 | Baskins et al. | 250/343 |
| 4,560,873 | 12/1985 | McGowan et al. | 250/339 |

Primary Examiner—Janice A. Howell
Assistant Examiner—Constantine Hannaher
Attorney, Agent, or Firm—Fitch, Even, Tabin & Flannery

[57] ABSTRACT

A gas analyzer is described comprising a sample cell for containing a gas mixture to be analyzed, a source for producing and directing infrared energy through the sample cell, a rotary filter wheel having at least one filter thereon for passing infrared energy limited to a wavelength band within the characteristic absorption band of a predetermined gas and having a dark level region substantially opaque to infrared energy, a drive for supporting and rotating the filter wheel to successively interpose the filter and the dark level region between the source and the sample cell in the path of the infrared energy directed by the source, a detector for detecting infrared energy passing through the sample cell and producing an electrical signal representative thereof, and a signal processor connected to the detector for producing an output indicating the concentration of the predetermined gas in the sample cell by comparing the electrical signals produced by the detector with the filter positioned in the infrared energy path and with the dark level region positioned in the infrared energy path. The dark level region has a substantially fully reflective surface oriented toward the sample cell when positioned in the infrared energy path whereby infrared energy impinging thereon is reflected.

6 Claims, 3 Drawing Figures

DIGITAL ANESTHETIC AGENT ANALYZER

This invention relates to infrared gas analyzers and, more particularly, to an improved infrared gas analyzer capable of high accuracy and fast response in connection with difficult to measure gases, yet still relatively low in cost.

Many types of infrared gas analyzers utilize an infrared source to produce and direct infrared energy through an unknown gas mixture contained in a sample cell. The energy passing through the sample cell is detected and electrical signals are produced representative thereof. These signals are processed to produce an output indicating the concentration of one or more of the constituents of the gas in the sample cell.

Such gas analyzers utilize the principle that various gases exhibit a substantial absorption characteristic at specific wavelengths in the infrared radiation spectrum. A gas analyzer of this type is shown and described in U.S. Pat. No. 4,013,260, McClatchie et al., issued Mar. 22, 1977, and assigned to the assignee of the present invention. Another type of infrared gas analyzer is shown and described in U.S. Pat. No. 3,953,734, Dimeff, issued Apr. 27, 1976, and assigned to the United States of America.

In both of the above cited patents, and in similar types of infrared gas analyzers, the wavelength band of the beam of infrared energy passing through the sample cell containing the unknown gas mixture is changed periodically by the interposition on one or more filters in the path of the light beam. Typically, each filter passes only radiation at a narrow band corresponding to a characteristic absorption wavelength band of a particular gas of interest. Another filter may also be used as a reference filter at a wavelength band close to but not substantially overlapping the characteristic absorption wavelength band of any of the gases present in the sample cell.

Gas analyzers of the foregoing described type usually continuously reference the radiation detected at the characteristic bands to radiation detected at reference levels (i.e., a non-absorbed wavelength and a dark or totally blocked level). By doing so, the effect of so-called drift is minimized, and the effect of background noise is reduced. Drift can occur as a result of contamination on the windows in the sample cell which will attenuate the radiation passing therethrough and which could be interpreted erroneously as indicating the presence of the gas to be detected in the gas sample. Drift can also be caused by shifts in the output of the detector, inherent in many detector constructions, and temperature changes in the source of the infrared radiation.

Gas analyzers of the foregoing described type, in spite of their high accuracies, still can experience error introduced by a variety of factors. One of such factors is variation in the temperature between different components of the gas analyzer. Temperature, of course, can often be stabilized through expedients such as heat sinks, coolers, etc. However, the use of such elements introduces significant cost increases which may be undesirable.

Another error factor is the presence of certain gases or combinations of gases in the sample cell having absorption bands which substantially overlap. For example, the absorption band of water vapor is very wide and may overlap the absorption band of other gases present in the sample cell. Without correcting for this, significant error can result. The very strong absorption characteristic of carbon dioxide may also cause errors in the observed measurements for other gases present where there is even a small overlap.

The effect of some temperature variations on accuracy can often be reduced by positioning the rotating filter wheel at the input side of the sample cell (i.e., between the infrared source and the sample cell) rather than at the outlet side (between the sample cell and the detector). Although certain other problems may be introduced by such positioning of the filter wheel, such positioning is preferred and the additional errors introduced by such positioning are often tolerable.

Nevertheless, for certain gases or gas mixtures, higher accuracy is needed than has been typically achieved in prior art devices without extraordinary expense. For example, in the measurement and monitoring of gases being administered to an anesthetized patient undergoing surgery, the patient's inhaled and exhaled gas mixture may include percentages of gases such as halothane, methoxyflurane, isoflurane and enflurane, as well as carbon dioxide and water vapor. The absorption characteristics of these various gases differ widely. For example, the absorption of carbon dioxide at its characteristic wavelength may be many times greater than the absorption of halothane at its characteristic absorption wavelength. Where the sample cell must be small, for fast response times in the analyzer, error correction becomes even more significant.

Accordingly, there remains a need, particularly in connection with the monitoring of anesthetic agents and associated gases, to provide a gas analyzer having a fast response time along with a high accuracy and stability at a reasonable price.

It is an object of the present invention to provide an improved gas analyzer.

Another object of the invention is to provide a gas analyzer of high accuracy and stability which is relatively low in cost.

Another object of the invention is to provide a gas analyzer which is particularly well-suited to use in connection with the measurement of gases in inspired and expired gases of a patient under anesthesia.

Other objects of the invention will become apparent to those skilled in the art from the following description, taken in connection with the accompanying drawings wherein.

Very generally, the gas analyzer of the invention comprises a sample cell for containing a gas mixture to be analyzed. Infrared energy from a source is directed through the sample cell. A rotary filter wheel having at least one filter thereon for passing infrared energy at a wavelength band within the characteristic absorption band of a predetermined gas. The filter wheel is also provided with a dark level region substantially opaque to infrared energy. The filter wheel is supported and rotated to successively interpose the filter and the dark level region between the source and the sample cell in the path of the infrared energy directed by the source. Infrared energy passing through the sample cell is detected and an electrical signal is produced representative of the amplitude of the infrared energy. The electrical signal is processed to produce an output indicating the concentration of the predetermined gas in the sample cell. During the processing, the electrical signals produced by the detector with the filter positioned in the infrared energy path are compared with the signals produced when the dark level region is positioned in the infrared energy path. The dark level region has a substantially fully reflective surface oriented toward the sample cell when positioned in the infrared energy path. Accordingly, the infrared energy impinging on the dark level region is reflected substantially toward the detector.

Figure 1:
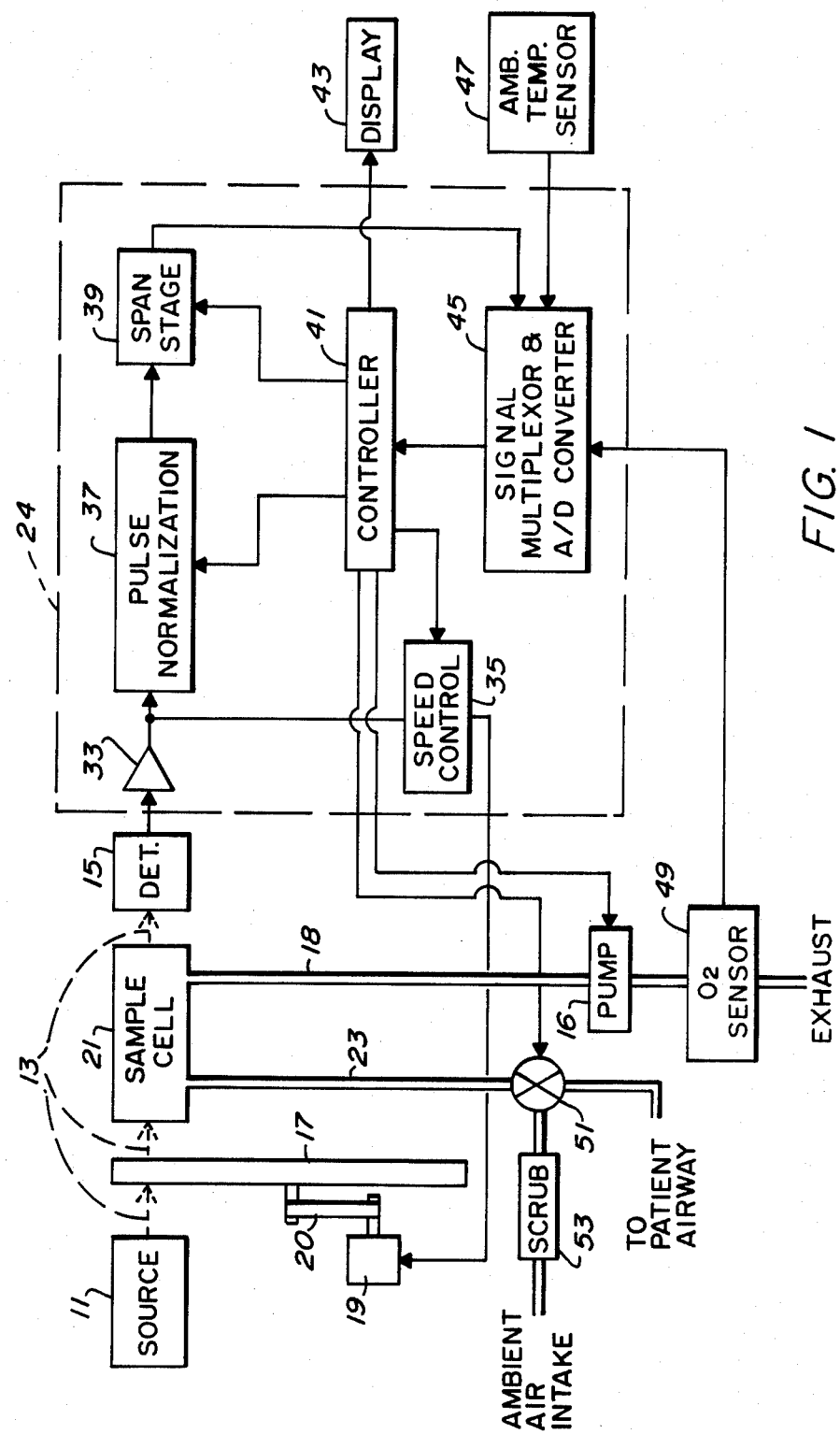
FIG. 1 is a block diagram of an infrared, non-dispersive gas analyzer incorporating the invention.

Now referring to FIG. 1, a block diagram of the system of the present invention may be seen. An infrared source 11 of any suitable construction is located at one end of an infrared optical path 13 which terminates at the other end at a detector 15. In line in this optical path is a rotating filter wheel 17, which may be rotated by a motor 19 and belt drive 20 about an axis parallel to but offset from the optical path. Also in the optical path is a sample cell 21 into which the gas mixture to be analyzed is passed. For example, in the case of monitoring the intake and expiration of breath in a patient under anesthesia, the sample cell may be connected through a tube 23 to airway tubing attached to the patient.

In order to exhaust the sample gases from the sample cell 21, an exhaust tube 18 is provided which communicates through a pump 16. Periodic operation of the pump 16 can supply sample gas to the sample cell 30 through the inlet tube 23.

A signal processor 24 is provided to process the output signals developed by the detector 15, which are synchronized with the position of the rotating filter wheel 17 to provide a plurality of measurements as described below. The rotating filter wheel may, for example, be driven directly, or by an appropriate 3450 RPM non-synchronous motor through a suitable drive belt or gear arrangement, not shown, so as to rotate at a speed of approximately 6,000 RPM.

Figure 2:
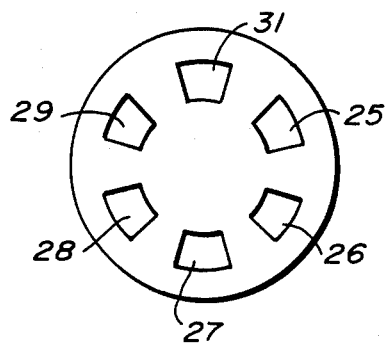
FIG. 2 is a plan view of the filter wheel utilized in the gas analyzer of FIG. 1.

The rotating filter wheel itself is better illustrated in FIG. 2, which schematically illustrates the face of the rotating filter wheel of the preferred embodiment. The rotating filter wheel is shown separated into six segments of sixty degrees each, with four of the six segments containing filters 25 through 29 and with the sixth angular segment being occupied by a solid portion of the wheel. Other combinations and numbers, however, could be used without departing from the scope of this invention. As will be subsequently shown, the filters 25 through 29 are each selected to pass narrow bands of infrared radiation, each having different band centers at predetermined wavelengths to provide four measuring signals and one reference signal. The sixth angular segment or region 31 of the wheel does not have a filter and is utilized to block the source radiation from the sample cell so that the detector signal may be used to indicate combined effects such as background radiation, detector null, electronics offset, etc. (i.e., background noise).

The sample cell 21 contains the gas mixture to be analyzed. The gas mixture includes a gas of interest being a selected one of a plurality of gases. Each of the gases has an absorption characteristic associated therewith, as below described. As the infrared energy passes through cell 21, the gas mixture absorbs a portion of such energy.

The detector 15 is responsive to the infrared energy passing through the cell 21. As each pulse of energy is passed by a filter in the filter wheel 17, a signal pulse is developed by the detector. Each pulse has an amplitude determined by the radiant energy passing through the cell 21 at the particular wavelength of the filter then interposed in the energy path. The pulse is applied to the signal processor 24.

Figure 3:
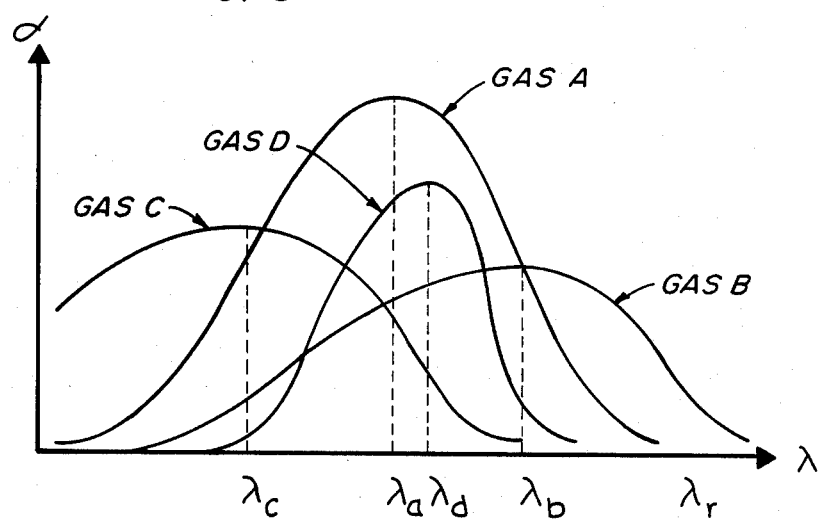
FIG. 3 is a graph illustrating the absorption characteristics of various gases which may be monitored with the invention.

Referring now to FIG. 3, there is shown, as an example only, an absorption ($\partial$) versus wavelength ($\lambda$) representation illustrating a possible absorption characteristic for four gases A, B, C, and D, respectively. Each of gases A, B, C, and D has a characteristic absorption wavelength $\lambda_a$, $\lambda_b$, $\lambda_c$, $\lambda_d$, respectively. The absorption of infrared energy passing through the sample cell is at the characteristic absorption wavelength $\lambda_a$–$\lambda_d$ (determined by the fiters) of the respective one of gases A–D. The characteristic absorption being all wavelengths at which a gas absorbs infrared energy. One preselected wavelength $\lambda_r$ (the reference filter) is chosen to be outside all of the absorption characteristics of gases A–D as shown in FIG. 3.

The gas analyzer of the present invention is particularly useful for analyzing the expired breath of a patient under anesthesia. Typical conditions will include carbon dioxide, water vapor, nitrous oxide, oxygen, and one or more of the previously mentioned anesthetic agent gases, such agents having a concentration in the expired breath of one to five percent or less typically. Each of these anesthetic agents absorbs infrared energy at a wavelength of about 3.3 microns.

The basic theory of operation of the system is as follows: The detector signal measured when the reference filter (wavelength $\lambda r$) is aligned in the optical path provides a measure of the basic sensitivity of the system to infrared radiation in general. That is, it provides a measure of the strength of the radiation of the infrared source, the attenuation of the radiation by {non-spectral} contamination and the like on the infrared transparent windows in the sample cell, and further provides a measure of the effectiveness of the collector and the sensitivity, of the detector as well as the gain of the processing electronics. Each of the other filters ($\lambda a$–$\lambda d$) provide radiation which ideally can only be absorbed, if at all, by the presence of the specific gas (A–D) to be detected having an absorption characteristic corresponding to that filter. Of course, contamination on the windows, variations in the source radiation, detector characteristics, etc. will also vary the signal received, which sensitivity may be minimized by the use of the reference signal which is similarly affected.

In practice, for an evacuated sample cell, or in the alternative for a sample cell containing gases other than the gases to be detected, the detector signal versus rotating filter wheel angular position will be different. This is because of such effects as different optical characteristics of the filters, and source radiation and detector wavelength sensitivities. The four signals received will be of different amplitudes.

Difference in signal amplitude could be equalized optically, by controlling the aperture of each reference filter, or electronically by sampling the smaller signals for a longer time with a circuit sensitive to the time amplitude characteristics rather than mere amplitude or amplitude-fixed time product characteristic of the sensing. This is difficult, however, because such mechanical changes involve costly mechanical complexities and time consuming adjustment, and the fixed sample time circuits are by far the easiest to fabricate and use.

Another method of equalizing the signals would be to add an appropriate bias voltage to each of the signals to bring all of the signals up to predetermined level. This, however, would still result in a system which was sensitive to optical characteristic changes, since if the optical windows collected contamination so as to drop all signal strengths by twenty percent, the bias voltage would not drop accordingly, and the four signals would no longer be equal when the sample cell was free of the gas to be detected. This would result in various output signals in a condition when no output signals should be present.

In the preferred embodiment, the detector signals for each of the five filters are measured for a predetermined angle of the filter wheel, utilizing a system having a different gain for each of the sensed signals predetermined to equalize the signals when none of the gases to be measured are present in the sample cell. Thus, variations in intensity of the radiation in the optical system caused by contamination on the sample cell windows, etc. will generally vary all signals in proportion so that the four gas signals and the reference signal will track each other with a high degree of accuracy.

In furtherance of the foregoing objective, it should be noted that there is a certain amount of background radiation present in any such system. This is radiation which will be incident upon the detector even when the infrared radiation source is off, or blocked from radiating into the sample cell by the solid portion of the rotating filter assembly. Other signals are also present which are functionally equivalent to the background radiation, such as possible null output of the detector, input offsets in the electronics, etc. These signals typically do not vary with variations in source intensity, window transmissibility, etc., and accordingly should be removed from all signals before the gain adjustment is made to equalize the outputs.

In some cases the wavelength of the reference filter will not be entirely outside the absorption band of all gases present in the sample cell. In these instances, some gain compensation may be needed which can be calculated and compensated for in the signal processor more particularly described below.

Returning now to FIG. 1, the signal processor 24 includes a preamplifier 33 connected to the output of the detector. A feedback loop extends from the output of the preamplifier 33 through a speed control circuit 35 to the motor 19 to stabilize the motor speed. The output of the detector 33 is also applied to a pulse normalization circuit 37 the output of which, in turn, is applied to a span stage circuit 39.

The pulse normalization circuit 37 operates to adjust the amplitude of the pulses output by the preamplifier 33 from the detector 15 to a standard or predetermined amplitude in the absence of a gas in the sample cell which absorbs at the particular wavelength of that pulse. The span stage 39, on the other hand, adjusts the gain of each pulse in accordance with the absorption characteristics of the gas corresponding to that particular wavelength. The gain of each pulse channel is selected so that a full pulse in the absence of any gas absorbing at that particular wavelength will be at a standard output voltage. Circuits for achieving pulse normalizations and span stage adjustment are well known in the art and will not be described with greater particularity herein. Any suitable pulse normalization circuit or span stage adjustment circuit may be utilized within the scope of the present invention.

Operation of the pulse normalization circuit 37 and the span stage adjustment circuit 39 are controlled by a controller 41. The controller 41 may be any suitable microprocessor based controller and preferably contains memory for storing such information as filter parameters, gas absorption characteristics, etc. The particular program upon which the microprocessor operates is also preferably stored internally in a suitable ROM.

The output of the controller 41 is applied to a suitable display 43. The display 43 may comprise dials, digital displays or other appropriate indications of the concentrations of the gases of interest in the sample cell. The microprocessor controller 41 may also be controlled or its programs otherwise modified by means of an external operator keyboard, not shown.

Various operating conditions sensed by appropriate sensing devices, only some of which are illustrated, are applied to the controller 41 by a signal multiplexer and analog-to-digital convertor 45. For example, the ambient temperature may be sensed by an ambient temperature sensor 47, which provides an analog output to the circuitry 45 which is then appropriately converted to corresponding digital information. Similarly, oxygen present at the exhaust tube 18 of the sample cell 21 may be sensed by an oxygen sensor 49 which applies an analog output to the circuitry 45. After multiplexing, the signals representing oxygen concentration and ambient temperature are then applied to an analog-to-digital converter and provided to the controller 41 for further processing.

A valve 51 is provided in the inlet tube 23. The valve 51 operates to close off the connection to the patient airway and to interconnect an ambient air intake and scrubber 53 to the inlet tube 23. When this is done, operation of the pump 16 purges the sample cell of all gases therein and replaces those gases with ambient air which has been scrubbed of carbon dioxide. When this is done, the controller can then adjust the pulse normalization stage 37 to recalibrate the normalization adjustments.

In operation of the device, output pulses from the detector 15 are amplified in the preamplifier 33 and are then adjusted in the pulse normalization circuit 37. The pulse normalization circuit adjusts the amplitude of the pulses in accordance with variations in the amplitude of the reference filter pulses, thereby eliminating drift caused by window contamination, etc.

In the span stage 39, the signal is once more adjusted to scale the pulses in accordance with the different absorption characteristics of the gases being measured. For example, the amplitude of the absorption caused by carbon dioxide may be many times higher than that caused by typical anesthetic agent gases. The span stage 39 permits these variations to be properly scaled.

As previously mentioned, various error causing factors can sometimes be eliminated by relatively expensive features in gas analyzers. One such error causing factor is that the dark level sensed by the detector during the time that the region 31 is positioned in the optical path may vary. Variations in dark level are caused by background infrared radiation from a variety of sources and is of course present continuously in the system. It has been discovered that variations in the background level can occur depending on whether a filter is in the infrared energy path or whether the infrared energy path is blocked. This is because typical prior art devices block the infrared radiation by the interposition of an opaque portion of the filter wheel. Typically, the surface of the filter wheel absorbs or emits infrared radiation but does not reflect it. On the other hand, typical filter materials will, in addition to acting as windows to infrared radiation, also cause some reflection of such radiation. The difference between the absorption emission phenomenon and the reflection phenomena can result in a different background depending upon whether a filter is in the infrared path or whether the infrared path is blocked. This can result in a change in the pulse height which is spurious (i.e., which is not caused by a change in the measured gas at the pulse wavelength) because any gas other than the measured gas can produce different absorptions of the different backgrounds and so produce apparent changes in the transmitted pulse that are large compared with the absorption of the characteristic radiation by the gas being measured.

Although this problem could be eliminated by placing the filter wheel at the side of the sample cell adjacent the detector, such repositioning introduces other undesirable problems. In accordance with the invention, the variation in dark level problem described above is eliminated by making the opaque section of the filter wheel, indicated at 31 in FIG. 2, reflective to infrared radiation. Any suitable reflective material may be utilized. By employing such material, variations in the background in the presence of the opaque region of the filter wheel in the radiation path versus filters interposed in the radiation path is eliminated.

As a further improvement from the above feature, the reflective surface of the opaque region 31 is positioned in the same plane as the reflective surface of the filters 25 through 29. By doing this, the average angle of the rays of light reflected from the opaque region is the same as that for the filters. This problem can be particularly acute where so called light pipe optics are utilized in the sample cell in order to maximize the path of light traveling through the cell. In other words, where the light rays are permitted to bounce off of the walls of the cell, rather being focused or collimated to pass cleanly through it, the path is lengthened for better response. However, because of the variation in light angles due to reflection from the walls of the sample cell and from the filters and opaque region on the filter wheel, the importance of having the reflective plane on the filter wheel uniform is significantly increased.

Problems in accuracy in gas analyzers of the type to which the present invention relates are also introduced due to the presence of water vapor in the sample cell. This is particularly acute when the gases of interest include gases which have only a very low absorption, which is typical of halothane. Water vapor will have an absorption characteristic which interferes with some gases but not of others.

In accordance with the invention, a filter is utilized in the filter wheel 17 as a reference filter which will transmit two wavelengths. The two wavelengths passed by the filter are selected so that one wavelength is completely out of the absorption zone of water vapor and so that another wavelength is completely in the absorption zone of water vapor. Both wavelengths are selected to be out of the absorption regions of any other gases expected to be present in the sample cell. By selecting the appropriate wavelengths, and by adjusting the amplitude of the infrared energy passed through the filter at those wavelengths, the variation in absorption of the other wavelengths of interest due to the presence of water vapor may be tracked perfectly by the dual wavelength reference filter. Such dual wavelength reference filters are available from Barr Associates, Massachusetts, U.S.A. By utilizing a single dual wavelength filter as above described, or a combination of two or more filters in series, optically, it is possible to compensate for the presence of water vapor without adding extra channels with consequent greater expense in the filer wheel and in the signal processing circuitry.

As previously mentioned, the use of so called lightpipe optics in the sample cell produces longer path lengths for the radiation and is therefore preferable where a fast response time (with lower sample cell size) is desired. It has been discovered, however, that typical materials employed for reflective surfaces for infrared radiation, such as polished aluminum, are highly adsorbent to water molecules. These water molecules are adsorbed (not condensed) on the walls of the sample tube, introducing error because of the wide band and variable absorption characteristics of water molecules. Materials which have a low adsorption for water molecules, such as stainless steel, are not highly reflective for infrared radiation and therefore are not satisfactory. It is possible to heat the sample cell to break the adsorption band of the water molecules on the walls, but such high temperatures (400° to 500° C.) are required as to make this impractical.

In accordance with the invention, materials have been found which are sufficiently reflective to infrared radiation as to be capable of being employed in the sample cell, but which are sufficiently low in adsorption affinity for water molecules as to prevent the above described problem. Such materials include silicon oxide, magnesium fluoride and gold.

Another error factor which may be present in a gas analyzer results from the presence of ambient air in the radiation path in the spaces between the various elements of the gas analyzer. Since the ambient air present may be different in certain gas concentrations from that present in the sample cell, and since ambient air can change with time after calibration of the instrument, error can result. Such error could be eliminated by filling the ambient air spaces or evacuating those spaces, but such expedients introduce significant expense.

In accordance with a further feature of the invention, a sealed gas cell is placed in the optical path filled with a fixed amount of carbon dioxide. The amount of carbon dioxide is selected to absorb sixty to seventy percent of the infrared radiation in the region of the carbon monoxide characteristic absorption wavelength band. At lower radiation intensity levels, the behavior of carbon dioxide more closely approximates the behavior of the other gases present in the sample cell and which are of interest. This reduces the overall sensitivity of the instrument to the presence of ambient air in the infrared energy path.

As previously mentioned, the gas analyzer of the invention contains an automatic zeroing function. As a further feature of the present invention, this automatic zeroing is triggered upon the occurrence of three sensed conditions. The first of these conditions is time. The controller 41 is provided with a suitable internal clock, not shown, to produce an automatic zeroing instruction a predetermined time after warmup of the device. Such a predetermined time may, for example, be thirty minutes and is for the purpose of recalibrating the device once the various parts of the device have warmed up to their typical operating conditions. After warmup, the temperature levels of various parts can be significantly different than those existing immediately after a cold start.

In addition, the controller 41 is set to initiate automatic zeroing upon a predetermined change in ambient temperature. A change in ambient temperature can have a significant effect on the relative temperatures of the various parts and therefore on the accuracy of the device. An initiation of automatic zeroing upon sensing a change in ambient temperature of about five to ten degrees is typically preferred.

Finally, automatic zeroing is initiated by the controller 41 upon the sensing of a predetermined change in the amplitude of the pulse in the reference filter. A preferred level is of the order of 0.2 percent change. Such a rezeroing will recalibrate the device where significant changes have occurred in background conditions.

All of the foregoing features contribute, collectively, to a significant improvement in the stability and accuracy of the gas analyzer of the invention at a relatively modest cost as compared with what is taught by the prior art. This is because such expedients permit the use of less stable but cheaper parts in critical areas in the gas analyzer.

It may be seen, therefore, that the invention provides an improved gas analyzer which is particularly suited to the monitoring of anesthetic agents and associated gases. The analyzer of the invention has a fast response time along with a high accuracy and stability and yet may be constructed at a reasonable price. Various modifications of the invention will become apparent to those skilled in the art from the foregoing description and accompanying drawings. Such modifications are intended to fall within the appended claims.

What is claimed is:

1. A gas analyzer comprising, a sample cell for containing a gas mixture to be analyzed, source means for producing and directing infrared energy through said sample cell, a rotary filter wheel having at least one filter thereon for passing infrared energy limited to a wavelength band within the characteristic absorption band of a predetermined gas and having a dark level region substantially opaque to infrared energy, drive means for supporting and rotating said filter wheel to successively interpose said filter and said dark level region between said source means and said sample cell in the path of the infrared energy directed by said source means, detector means for detecting infrared energy passing through said sample cell and producing an electrical signal representative thereof, signal processing means connected to said detector means for producing an output indicating the concentration of the predetermined gas in the sample cell by comparing the electrical signals produced by said detector means with said filter positioned in the infrared energy path and with said dark level regions positioned in the infrared energy path, said filter wheel including a second filter for passing first and second infrared wavelength bands, one of which is within a region of infrared absorption by water vapor and the other of which is not, both of said first and second wavelength bands of said second filter being outside the characteristic wavelength absorption regions of other gases present in the sample cell, the amplitude of transparency of said second filter at each of said first and second infrared wavelength bands being selected to track the variation in absorption of infrared energy at the wavelength of said first filter due to the presence of water vapor in said sample cell.

2. A gas analyzer according to claim 1 wherein said dark level region has a substantially fully reflective surface oriented toward said sample cell when positioned in the infrared energy path such that infrared energy impinging thereon is reflected and wherein said reflective surface of said dark level region is positioned in substantially the same place of rotation as the side of said filter facing said sample cell.

3. A gas analyzer according to claim 1 wherein the interior surfaces of said sample cell are comprised substantially of a material having a low affinity for, bonding with water molecules.

4. A gas analyzer according to claim 3 wherein said material is selected from the group consisting of silicon oxide, magnesium fluoride and gold.

5. A gas analyzer according to claim 1 including means for sensing the ambient temperature and for activating said automatic zeroing means upon a change in ambient temperature said source of a predetermined amount.

6. A gas analyzer according to claim 1 including a reference filter in said filter wheel, said signal processing means including means for comparing the level of infrared energy passing through said sample cell when said filter is interposed in the path of infrared energy and when said reference filter is interposed in the path of the infrared energy, means for monitoring the amplitude of the signal detected by said detector means with said reference filter interposed in the path of infrared energy and for activating said automatic zeroing means upon a change in the level of said signal of a predetermined amount.

* * * * *

UNITED STATES PATENT AND TRADEMARK OFFICE
CERTIFICATE OF CORRECTION

PATENT NO. : 4,692,621
DATED : September 8, 1987
INVENTOR(S) : Robert E. Passaro, et al.

It is certified that error appears in the above-identified patent and that said Letters Patent is hereby corrected as shown below:

On the title page

At [73], Assignee's name is misspelled.
"ANLAYZERS" should be --ANALYZERS--.

Signed and Sealed this

Eleventh Day of October, 1988

*Attest:*

DONALD J. QUIGG

*Attesting Officer*    *Commissioner of Patents and Trademarks*